United States Patent [19]

Lassen

[11] 4,038,395
[45] July 26, 1977

[54] COMPOSITIONS OF AND METHOD OF TREATING WITH THE ALPHA-ISOMER OF 2-CHLORO-9-[3'-(N'-2-HYDROXYETHYL-PIPERAZINO-N)-PROPYLIDENE]-THIAX-ANTHENE, CARBOXYLIC ACID ESTERS THEREOF AND ACID ADDITION SALTS OF THESE COMPOUNDS

[75] Inventor: Niels Lassen, Gentofte, Denmark

[73] Assignee: Kefalas A/S, Copenhagen-Valby, Denmark

[21] Appl. No.: 696,800

[22] Filed: June 16, 1976

Related U.S. Application Data

[62] Division of Ser. No. 479,814, June 17, 1974, Pat. No. 3,996,211.

[30] Foreign Application Priority Data

June 25, 1973  United Kingdom ............... 30152/73

[51] Int. Cl.$^2$ .......................................... A61K 31/495
[52] U.S. Cl. ..................................................... 424/250
[58] Field of Search ................................:.......... 424/250

*Primary Examiner*—Stanley J. Friedman
*Attorney, Agent, or Firm*—Gordon W. Hueschen

[57] ABSTRACT

The present invention relates to the novel alpha-isomer of 2-chloro-9-[3'-(N'-2-hydroxyethylpiperazino-N)-propylidene]-thiaxanthene, carboxylic acid esters thereof, the non-toxic acid addition salts of these compounds, methods of preparing and purifying the said compounds, therapeutic compositions thereof and a method of treating psychotic patients therewith.

20 Claims, No Drawings

COMPOSITIONS OF AND METHOD OF TREATING WITH THE ALPHA-ISOMER OF 2-CHLORO-9-[3'-(N'-2-HYDROXYETHYL-PIPERAZINO-N)-PROPYLIDENE]-THIAXANTHENE, CARBOXYLIC ACID ESTERS THEREOF AND ACID ADDITION SALTS OF THESE COMPOUNDS

This is a division of application Ser. No. 479,814, filed June 17, 1974, now U.S. Pat. No. 3,996,211.

BACKGROUND OF THE INVENTION

The compound 2-chloro-9-[3'-(N'-2-hydroxyethylpiperazino-N)-propylidene]-thiaxanthene has for some years, in the form of a mixture of the cis-trans isomers, proved a valuable neuroleptic drug in the treatment of psychotic disorders, mostly schizophrenic patients.

The compound, which in the following is called clopenthixol (CPT) for short, is effective in doses of from about 5 mg to about 25 mg per unit dosage. Clopenthixol is preferably used in the form of acid addition salts, such as the dihydrochloride, in oral unit dosage forms. When clopenthixol is prepared according to the method described in U.S. Pat. No. 3,116,291 a mixture of isomers is obtained wherein approximately 35%, mostly about 30-50%, of the most active isomer (for convenience called alpha-clopenthixol) is present.

A separation of the isomers along the lines described in U.S. Pat. No. 3,116,291 failed to succeed. When fractional crystallization of either the free base or an acid addition salt thereof in various solvents was attempted the inactive beta-isomer being the most insoluble always crystallized out first, and from the mother liquors resulting from the crystallizations only mixtures of the alpha- and beta- isomers were obtained.

SUMMARY OF THE INVENTION

It has now according to one method of the invention surprisingly been found that by benzoylation of the residue obtained from the crystallization of the beta-isomer and crystallization of the resulting mixture of the benzoic acid esters of the alpha- and beta-isomers the pure benzoic acid ester of the alpha-isomer of clopenthixol crystallized out. From this ester the pure alpha-isomer could easily be obtained by a conventional saponification or reduction with lithium aluminium hydride.

Accordingly, the method of preparing and purifying the pure alpha-isomer of 2-chloro-9-[3'-(N'-2-hydroxyethylpiperazino-N)-propylidene]-thiaxanthene is characterized thereby that from a mixture of isomers containing from about 30-50% of the alpha-isomer most of the beta-isomer is removed by crystallization from an organic solvent, the mother liquor evaporated, the residue benzoylated with an active benzoic acid derivative, such as the anhydride, chloride, bromide or the like, the resulting mixture of isomeric benzoic acid esters subjected to crystallization from an organic solvent, and the resulting benzoic acid ester of the pure alpha-isomer saponified or was reduced in wellknown manner to yield the pure alpha-isomer which is isolated as such or in the form of a non-toxic acid addition salt thereof, or, if desired, the pure alpha-isomer is acylated with a reactive derivative of a carboxylic acid having from one to sixteen carbon atoms inclusive, and the resulting ester isolated as such or in the form of an addition salt thereof with a pharmaceutically acceptable acid.

The solvents used for the crystallizations may be alcohols such as methanol, ethanol, propanol, n-butanol, or the like, ketones such as acetone, methyl iso-butyl ketone, or the like, or ethers such as diethyl ether, diisopropyl ether, or the like. Other solvents may, however, be used as well. Preferably, however, ethers such as diethyl ether or diisopropyl ether are used.

The reactive carboxylic acid derivatives used for the esterification according to the invention are preferably from aliphatic carboxylic acids, for example, acetic acid, propionic acid, iso-propionic acid, valeric acid, caproic acid, enanthic acid, decanoic acid, plamitic acid, and the like. Especially the esters of higher carboxylic acids, such as enanthic acid, decanoic acid palmitic acid have proved valuable in the form of oily solutions for injection, said oily solutions having a prolonged effect as compared with the unesterified alpha-isomer of clopenthixol.

As non-toxic acid addition salts of the novel alpha-isomers of the invention may be mentioned the hydrochlorides, hydrobromides, sulphates, acetates, phosphates, nitrates, quinates, methanesulphonates, ethanesulphonates, lactates, citrates, tartrates, bitartrates, maleates, benzoates, ascorbates, embonates, salicylates, and the like.

The following examples illustrate the method of the invention but may not be construed as limiting:

EXAMPLE 1

The alpha-isomer of 2-chloro-9-[3'-(N'-2-hydroxyethylpiperazino-N)-propylidene]-thiaxanthene, the benzoic acid ester thereof and the dihydrochloride.

100 grams of a mixture of isomers of 2-chloro-9-[3'-(N'-2-hydroxyethylpiperazino-N)-propylidene]-thiaxanthene (containing 35% of the alpha-isomer) in the form of an oil were dissolved in 500 milliliters of isopropyl ether. Upon standing 50 grams of the beta-isomer melting at 100°-102° C. crystallized out and were sucked off. The mother liquor was evaporated and the residue dissolved in 300 milliliters of dry acetone. To the solution were added 20 grams of benzoyl chloride and the mixture heated under reflux for 10 minutes. After cooling a solution of dry hydrogen chloride in ether was added to pH 3. The precipitate which consisted of a mixture of the isomeric benzoic acid esters was sucked off and treated with 1 liter of a 10% aqueous solution of sodium carbonate and thereafter shaken with 500 milliliters of ether until all had gone into solution. The ether phase was separated, dried over anhydrous potassium carbonate, filtered and evaporated to a volume of about 200 milliliter. Upon cooling 30 grams of the benzoic acid ester of the alpha-isomer of clopenthixol crystallized out. Upon recrystallization from ether it melts at 101°-103° C.

The ester was saponified by heating on a steam bath with a solution of 10 grams of potassium hydroxide in 100 milliliters of ethanol for 15 minutes. After cooling the mixture was poured into water and extracted with ether. The ether solution was dried over anhydrous potassium carbonate, filtered and evaporated to about 150 milliliters. Upon standing and cooling 20 grams of the pure alpha-isomer of 2-chloro-9-[3'-(N-2-hydroxyethylpiperazino-N)-propylidene]-thiaxanthene crystallized out. The crystals were sucked off and dried. MP 84-85 degrees Centigrade.

The dihydrochloride was prepared from a solution of the base in ethanol by addition of anhydrous hydrogen chloride and is a white crystalline substrate which melts at 250°–260° C. with decomposition.

The benzoic acid ester of the pure alpha-isomer may also be reduced with 2.5 grams of lithium aluminium hydride from a solution in dry ether by heating under reflux for 30 minutes. After cooling was added dropwise sufficient water to make the precipitate settle down whereupon the ether solution was decanted. The ether solution was treated as mentioned above.

EXAMPLE 2

The decanoic acid ester of the alpha-isomer of 2-chloro-9-[3'-(N'-2-hydroxyethyl-piperazino-N)-propylidene]-thiaxanthene and its dihydrochloride.

50 grams of the alpha-isomer of 2-chloro-9-[3'-(N'-2-hydroxyethylpiperazino-N)-propylidene]-thiaxanthene were dissolved in 250 milliliters of dry acetone. Then 26 grams of decanoyl chloride were added, whereupon the mixture was heated on a steam bath under reflux for one hour. After cooling a solution of dry hydrogen chloride in ether was added to pH 3. The crystalline precipitate was filtered off and washed with acetone. 71 grams of the dihydrochloride of the decanoic acid ester of alpha-isomer of 2-chloro-9-[3'-(N'-2-hydroxyethylpiperazino-N)-propylidene]-thiaxanthene were obtained as a white crystalline substance melting at 180°–190° C.

Alpha-clopenthixol or an ester thereof and the non-toxic acid addition salts thereof (in the following collectively called "active ingredients") may be administered to animals such as dogs, cats, horses, sheeps or the like, including human beings, both orally and parenterally, and may be used for example in the form of tablets, capsules, powders, syrups or in the form of the usual sterile solutions for injection. Results upon administration to human beings have been very gratifying.

Most conveniently the active ingredient is administered orally in unit dosage form such as tablets or capsules, each dosage unit containing a non-toxic acid addition salt of one of the said compounds in an amount of from about 1 to about 50 mg, most preferably, however, from about 5 to 25 mg, calculated as the free amine, the total daily dosage usually ranging from about 3 to about 300 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

Typical examples of formulas for compositions containing alpha-clopenthixol as the active ingredient are as follows:

1. Tablets containing 5 milligram of alpha-clopenthixol calculated as the free base in the form of the dihydrochloride:
   alpha-clopenthixol — 5 mg
   lactose — 37 mg
   potato starch — 74 mg
   gelatine — 2 mg
   talcum — 8 mg 2. Solution for injection containing per ml:
   alpha-clopenthixol — 5 mg
   sodium chloride — 9 mg
   sterile water — ad 1 ml 3. Syrup containing per milliliter:
   alpha-clopenthixol — 3 mg
   methyl-paraben — 1 mg
   propyl-paraben — 0.1 mg
   saccharose — 400 mg
   water — ad 1 ml 4. Capsules containing per capsule:
   alpha-clopenthixol — 10 mg
   lactose — 40 mg
   magnesium stearate — 0.5 mg Any other pharmaceutical tableting adjuvants may be used provided that they are compatible with the active ingredient, and additional compositions and dosage forms may be similar to those presently used for neuroleptics such as thiothixene, clopenthixol or flupenthixol. Also combination of the active ingredients as well as their non-toxic acid salts with other active ingredients especially other neuroleptics, thymoleptics, tranquilizers, or the like, fall within the scope of the present invention.

The invention further provides pharmaceutical compositions with prolonged action comprising, as active ingredient, the alpha-isomer of the decanoic acid ester of 2-chloro-9-[3'(N'-2-hydroxyethylpiperazino-N)-propylidene]thiaxanthene (called Lu 8–008 for short) or one of its non-toxic acid addition salts together with a pharmaceutical carrier or excipient.

They may be administered to animals including human beings both orally, parenterally and rectally and may take the form of e.g. sterile solutions or suspensions for injection, tablets, suppositories, capsules, and syrups.

Results upon administration to human beings of the compositions of the invention have been very gratifying. Preferably, however, the compositions are in the form of sterile solutions or suspensions for injection, and in a preferred embodiment of the invention injectable solutions may be prepared from a non-toxic injectable fat or oil, e.g. light vegetable oil, sesam oil, olive oil, arachis oil or ethyl oleate, and they may additionally contain gelling agents, e.g. aluminium stearate, to delay absorption within the body. Such oily solutions have a very prolonged activity when rejected intramuscularly, and satisfactory neuroleptic action has been produced by a single intramuscular injection of about 20 – 100 mg of Lu 8–008 dissolved in a light vegetable oil for as long as 2–4 weeks.

The following examples illustrate the injectable oily solutions according to the present invention:

| | | |
|---|---|---|
| 1. | Lu 8-008 | 50 grams |
| | sterile, light vegetable oil | ad 1000 ml |
| 2. | Lu 8-008 | 40 grams |
| | sterile sesam oil | ad 1000 ml |
| 3. | Lu 8-008 | 100 grams |
| | aluminium mono stearate | 20 grams |
| | sterile, light vegetable oil | ad 1000 ml |
| 4. | Lu 8-008 | 50 grams |
| | sterile olive oil | ad 1000 ml |

The solutions are filled in for example ampoules each containing 1 mg solution.

As previously stated, when isolating an active ingredient in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates or bitartrates, embonates and maleates of the active amines. Other acids are likewise suitable and may be employed if desired. For example fumaric, benzoic, ascorbic, succinic, salicylic, bismethylenesalicyclic, propionic, gluconic, malic, malonic, madelic, cinnamic, citraconic, stearic, palmitic, itaconic, glycolic, benzenesulphonic, and sulphamic acids may also be employed as acid addition saltforming acids. When it is desired to isolate a compound of the invention in the form of the free base, this may be done according to conventional procedure, as by dissolving the isolated or unisolated salt in water, treating with a suitable alkaline material, extracting the liberated free base with a suitable organic solvent drying the extract and evaporating to dryness or fractionally distilling to effect isolation of the free basic amines.

The invention also comprises a method for the alleviation, palliation, mitigation or inhibition of the manifestations of certain physiological-psychological abnormalies of animals by administering to a living animal body, including human beings, an adequate quantity of an active ingredient. An adequate quantity would be from about 0.005 mg to about 1 mg per kg of body weight in each unit dosage and from about 0.01 milligrams to about 3 milligrams/kg of body weight per day.

It is to be understood that the invention is not limited to the exact details of operation or exact compound or compositions shown and described, as obvious modifications and equivalents will be apparent to one skilled in the art.

Alpha-clopenthixol and its decanoic acid ester have been tested for neuroleptic activity with standard reliable test methods. In the testing alpha- and beta-clopenthixol (alpha-CPT and beta-CPT) have been compared with a sample of clopenthixol (CPT) containing 34% alpha-CPT as determined by I.R. spectrophotometry.

1. Inhibition of spontaneous motor activity in mice.

The method is described in Kopf, R. and I. Moller Nielsen: "Pharmakologische Eigenschaften einiger Phenylindolderivate". Arch.int.pharmacodyn. 1959, 119, 119–132.

Male mice (NMRI/BOM SPF) weighing 23–27 g were used throughout. When exposed to a new environment mice exhibit an increased exploratory activity, especially for the first 30 minutes.

In the pertinent experiments mice were placed in "jiggle-cages" 15 minutes after intraperitoneal drug administration, and the activity was recorded automatically for a period of 15 minutes. In the experiments performed there were used one mouse per cage, 10 mice per dose level and 20 mice in the control group. $DR_{50}$ is defined as the dose which reduces the activity to 50% of that of control mice. It should be noted that the damper of the oscillating cage has been supplied with a strain gauge transducer connected to an electronical system providing higher sensitivity than ever before. Results are shown in table 1.

Table 1

|           | $DR_{50}$ |
|-----------|-----------|
| alpha-CPT | 0.35      |
| beta-CPT  | 9         |
| CPT       | 0.75      |

2. Apomorphine antagonism in rats.

The test method used is a slight modification of the test described by Janssen, P.A.J., Niemegeers, C.J.E. and Schellekens, K.H.L., Arzneimittel-Forschung, 1965, 15, 104–117. Male rats (Wistar/Af/Han/Mo)(Han 67) SPF, 230–270 g) were given test substance intraperitoneally (9 animals per group). Two hours later apomorphine (10 mg/kg) was injected subcutaneously and the animals were placed in individual cages for one hour. A cage consisted of a 30 cm high perspex box (12 × 25 cm), without bottom and lid, which during the experiment was placed on corrugated paper. In this situation control animals, when given apomorphine, exhibit excessive gnaw-compulsion. In the experimental groups the percentage of animals that did not bite the corrugated paper was determined. Percentage non-biters was plotted on log-probit paper against dose and the $ED_{50}$ was read from the diagram.

The results are shown in table 2.

Table 2

| Compound  | Dose mg/kg i.p. | % Non-biters | $ED_{50}$ mg/kg i.p. |
|-----------|-----------------|--------------|----------------------|
| alpha-CPT | 10              | 100          |                      |
| 2 HCl     | 5               | 100          |                      |
|           | 2.5             | 44           | 2.4                  |
|           | 1.25            | 11           |                      |
| beta-CPT  | 80              | 11           |                      |
| 2 HCl     | 40              | 11           |                      |
|           | 20              | 0            | none                 |
|           | 10              | 11           |                      |
| CPT       | 20              | 78           |                      |
| 2HCl      | 10              | 67           |                      |
|           | 5               | 44           | 5.5                  |
|           | 2.5             | 33           |                      |

As it appears from the table alpha-CPT is 2–3 times more active than CPT. It also appears that beta-CPT is almost completely inactive in doses as high as 80 mg/kg i.p.

3. Methylphenidate antagonism in mice

Pedersen V. and A.V. Christensen: "Antagonism of methylphenidate-induced stereotyped gnawing in mice". Acta pharmacol. et toxicol. 1972, 31, 488–496.

Male mice (NMRI/BOM SPF, 18–25 g) were given an intraperitoneal dose of test compound. Two hours later 60 mg/kg of methylphenidate hydrochloride were injected subcutaneously, and immediately thereafter the animals were placed in cages, 2 mice in each cage, for 1 hour. The cages which during the experiment were placed on corrugated paper, are described under apomorphine antagonism on page 4. In this situation control mice, when given this dose of methylphenidate, will bite the corrugated paper (gnaw-compulsion). All compounds were tested at 5 dose levels using 5 pairs of mice per dose. Percentage non-biters was plotted on log.-probit paper against dose and approximate $ED_{50}$ values were read from the diagrams.

Results are shown in table 3.

Table 3

| Compound   | Dose mg/kg i.p. | % Non-biters | $ED_{50}$ mg/kg i.p. |
|------------|-----------------|--------------|----------------------|
| alpha-CPT, | 5               | 100          |                      |
| 2 HCl      | 2.5             | 100          |                      |
|            | 1.25            | 60           | 0.65                 |
|            | 0.63            | 60           |                      |
|            | 0.31            | 20           |                      |
| beta-CPT,  | 80              | 80           |                      |
| 2 HCl      | 40              | 80           |                      |
|            | 20              | 100          |                      |
|            | 10              | 20           |                      |
|            | 5               | 60           |                      |
| CPT,       | 10              | 100          |                      |
| 2 HCl      | 5               | 100          |                      |
|            | 2.5             | 80           | 1.2                  |
|            | 1.25            | 60           |                      |
|            | 0.63            | 20           |                      |

It appears that alpha-CPT is about twice as active as CPT (containing 34% alpha-CPT). With beta-CPT complete inhibition of methylphenidate-induced compulsive gnawing was obtained with 20 mg/kg, while as well higher as lower doses caused only partial inhibition (cf. table 2, apomorphine antagonism).

4. Acute toxicity

Acute toxicity upon intravenous injection has been tested using groups of five male mice (NMRI/BOM SPF, 18–25 g), fasted for 24 hours. Three or four dose-levels were needed to determine $LD_{50}$ values according to Miller and Tainter. Estimation of the $ED_{50}$ and its error by means of logarithmicprobit graph paper.

Table 4

| Compound | $LD_{50}$, mg/kg i.v. |
|---|---|
| alpha-CPT, 2HCl | 105 ± 10 |
| beta-CPT, 2 HCl | 134 ± 10 |
| CPT, 2 HCl | 111 ± 10 |

The results presented in table 4 indicate that the betaisomer is somewhat less toxic than the alpha-isomer and the mixture (34% alpha-CPT). There are, however, no statistically significant differences between the three $LD_{50}$ values.

5. Apomorphine antagonism in dogs

The prolonged neuroleptic effect of the decanoic acid ester of alpha-clopenthixol has been demonstrated in a test described by Janssen, P.A.J., Niemegeers, C.J.E. and K.H.L. Schellekens, Arzneimittel-Forschung, 1965, 15, 1196–1201.

It is generally accepted that antagonism to apomorphine is one of the most reliable criteria for predicting neuroleptic activity, the specific antipsychotic drugs being very strong apomorphine antagonists.

Adult purebred Beagles of either sex from our own stock were used. The threshold-dose of apomorphine for the provoking of vomiting in these dogs has been determined to 25 μg/kg i.v. After this dose vomiting occurs in a few minutes following the injection.

Four dogs were used for each dose level of the drug, which was injected subcutaneously at the back of the neck. At different times after the drug administration the dogs were then challenged with apomorphine according to an "up and down"-schedule using the dose-range 25–400 μg/kg i.v. geometrically spaced. Thus, if for example a dog vomited after 100 μg/kg, the next dog was given 50 μg/kg, or 200 μg/kg if the first dog did not vomit, and so on. In this way it was possible to estimate at which level of apomorphine the dogs were protected at a given time. The dogs were fed half an hour before testing to secure an easy vomiting act.

When 10 mg/kg clopenthixol 2 HCl was administered as an aqueous solution the effect abated rapidly, and when tested 4 hours p.i. maximal protection against apomorphine was afforded, and the effect was about 16 times the normal threshold level. It is to be emphasized that at this time and lasting for about 24 hours the dogs were heavily sedated and when left alone went asleep. The antagonism gradually vanished during the next two days, and at day 3 the protection was restricted to the threshold dose of apomorphine. At day 4 the dogs had returned to control level.

In contrast, when the same dose of 10 mg/kg was given as the depot-preparation (containing the alpha-isomer decanoic acid ester Lu 8–008, either 5 or 10% solution, a considerable prolongation of the protection against apomorphine can be seen. On the other hand, the maximally achieved level of protection was now only 2 and 4 times threshold dose of apomorphine for the 5 and 10% solutions, respectively.

This level was reached smoothly during the first week p.i., and then declined smoothly during the second week. It is noteworthy that in this case the dogs at no time displayed any signs of sedation.

Thus a prolongation from 3 to 14 days was obtained with the depot-preparation at this dose level.

Upon doubling the dose of Lu 8–008 to 20 mg/kg the protection was extended to 3 weeks with maximal effect of 8 times threshold during the first week. At this dose level the dogs become slightly sedated in the first week.

It was demonstrated that at both dose levels the 10% solution afforded a higher and/or more persisting maximal protection against apomorphine, although the duration was equal. Apparently, the 10% solution is better utilized in the body than the 5% solution.

I claim:

1. A pharmaceutical composition in unit dosage form, suitable for the use in the treatment of psychotic disorders, comprising a pharmaceutical carrier and an amount of a compound selected from the group consisting of (1) the alpha-isomer of 2-chloro-9-[3'-(N'-2-hydroxyethylpiperazino-N)-propylidene]-thiaxanthene, melting at 84°–85° C., substantially free of the beta-isomer, (2) a carboxylic acid ester thereof with from one to sixteen carbon atoms inclusive, and (3) an acid addition salt thereof with a pharmaceutically acceptable acid, which is effective for such purpose.

2. A composition according to claim 1, wherein the active ingredient is the dihydrochloride of the alpha-isomer of 2-chloro-9-[3'-(N'-2-hydroxyethylpiperazino-N)-propylidene]-thiaxanthene, melting at 250°–260° C. with decomposition.

3. A pharmaceutical composition in injectable form, suitable for use in the treatment of psychotic disorders, comprising as active ingredient an ester of the alpha-isomer of 2-chloro-9-[3'-(N'-2-hydroxyethylpiperazino-N)-propylidene]-thiaxanthene, melting at 84–85° C., substantially free of the beta-isomer, with a carboxylic acid having from one to sixteen carbon atoms inclusive, or an acid addition salt thereof with a pharmaceutically acceptable salt, together with a liquid pharmaceutically acceptable carrier therefor.

4. Composition according to claim 3, wherein the active ingredient is present in an amount of at least 1 milligram per milliliter.

5. A pharmaceutical composition in unit dosage form, suitable for use in the treatment of psychotic disorders, comprising a pharmaceutical carrier and an amount of a compound, selected from the group consisting of the decanoic acid ester of the alpha-isomer of 2-chloro-9-[3'-(N'-2-hydroxyethylpiperazino-N)-propylidene]-thiaxanthene and an acid addition salt thereof with a pharmaceutically acceptable acid, which is effective for such purpose.

6. A composition of claim 5, wherein the compound is the dihydrochloride of the decanoic acid ester of the alpha-isomer of 2-chloro-9-[3'-(N'-2-hydroxyethylpiperazino-N)-propylidene]-thiaxanthene, melting at 180°–190° C.

7. A composition of claim 5, wherein the compound is the decanoic acid ester of the alpha-isomer of 2-chloro-9-[3'-(N'-2-hydroxyethylpiperazino-N)-propylidene]-thiaxanthene.

8. A pharmaceutical composition in injectable form, suitable for use in the treatment of psychotic disorders, comprising as active ingredient a compound selected from the group consisting of the decanoic acid ester of the alpha-isomer of 2-chloro-9-[3'-(N'-2-hydroxyethylpiperazino-N)-propylidene]-thiaxanthene and an acid addition salt thereof with a pharmaceutically acceptable acid, together with a liquid pharmaceutically acceptable carrier therefor.

9. Composition of claim 8, wherein the active ingredient is present in an amount of at least about 0.5 mg.

10. A composition of claim 8, wherein the compound is the dihydrochloride of the decanoic acid ester of the alpha-isomer of 2-chloro-9-[(3'-(N'-2-hydroxyethylpiperazino-N)-propylidene]-thiaxanthene, melting at 180°–190° C.

11. A composition of claim 8, wherein the compound is the decanoic acid ester of the alpha-isomer of 2-chloro-9-[3'-(N'-2-hydroxyethylpiperazino-N)propylidene]-thiaxanthene.

12. A pharmaceutical composition of unit dosage form, suitable for use in the treatment of psychotic disorders, comprising a pharmaceutical carrier and an amount of the benzoic acid ester of the alpha-isomer of 2-chloro-9-[3'-(N'-2-hydroxyethylpiperazino-N)-propylidene]-thiaxanthene, melting at 101°–103° C., which is effective for such purpose.

13. A method for the treatment of psychotic disorders in mammals comprising the step of administering to the mammal an effective antipsychotic amount of a compound selected from the group consisting of (1) the alpha-isomer of 2-chloro-9-[3'-(N'-2-hydroxyethylpiperazino-N)-propylidene]-thiaxanthene, melting at 84°–85° C., substantially free of the beta-isomer, (2) a carboxylic acid ester thereof with from one to sixteen carbon atoms inclusive, and (3) an acid addition salt thereof with a pharmaceutically acceptable acid.

14. Method of claim 13, wherein the compound is administered in an amount of at least 0.5 mg.

15. Method of claim 13, wherein the compound is the dihydrochloride in the alpha-isomer of 2-chloro-9-[3'-(N'-2-hydroxyethylpiperazino-N)-propylidene]-thiaxanthene, melting at 250°–260° C. with decomposition.

16. A method for the treatment of psychotic disorders in mammals comprising the step of administering to the mammal an effective antipsychotic amount of an ester of the alpha-isomer of 2-chloro-9-[3'-(N'-2-hydroxyethylpiperazino-N)-propylidene]-thiaxanthene, melting at 84–85 degrees Centigrade, substantially free of the beta-isomer, with a carboxylic acid having from one to sixteen carbon atoms inclusive, or an acid addition salt thereof.

17. A method for the treatment of pyschotic disorders in mammals comprising the step of administering to the mammal an effective antipsychotic amount of a compound selected from the group consisting of the decanoic acid ester of the alphaisomer of 2-chloro-9-[3'-(N'-2-hydroxyethylpiperazino-N)-propylidene]-thiaxanthene and an acid addition salt thereof with a pharmaceutically acceptable acid.

18. A method of claim 17, wherein the compound is the dihydrochloride of the decanoic acid ester of the alpha-isomer of 2-chloro-9-[3'-2-hydroxyethylpiperazino-N) propylidene]-thiaxanthene, melting at 180°–190° C.

19. A method of claim 17, wherein the compound is the decanoic acid ester of the alpha-isomer of 2-chloro-9-[3'-(N'-2-hydroxyethylpiperazino-N)-propylidene]-thiaxanthene.

20. A method for the treatment of psychotic disorders in mammals comprising the step of administering to the mammal an effective antipsychotic amount of a compound which is the benzoic acid ester of the alpha-isomer of 2-chloro-9-[3'-(N'-2-hydroxyethylpiperazino-N)-propylidene]-thiaxanthene, melting at 101°–103° C.

* * * * *